(12) United States Patent
Lu et al.

(10) Patent No.: US 10,172,812 B2
(45) Date of Patent: Jan. 8, 2019

(54) COMPOUNDS AND METHODS FOR TREATING MUSCULAR DYSTROPHY AND OTHER DISORDERS

(71) Applicant: The Charlotte Mecklenburg Hospital Authority, Charlotte, NC (US)

(72) Inventors: Qi Long Lu, Charlotte, NC (US); Bo Wu, Matthews, NC (US)

(73) Assignee: The Charlotte Mecklenburg Hopital Authority, Charlotte, NC (US)

( * ) Notice: Subject to any disclaimer, the term of this patent is extended or adjusted under 35 U.S.C. 154(b) by 0 days.

(21) Appl. No.: 15/880,283

(22) Filed: Jan. 25, 2018

(65) Prior Publication Data

US 2018/0207112 A1 Jul. 26, 2018

Related U.S. Application Data

(60) Provisional application No. 62/450,451, filed on Jan. 25, 2017.

(51) Int. Cl.
| | |
|---|---|
| *A61K 31/138* | (2006.01) |
| *A61K 45/06* | (2006.01) |
| *A61K 31/4535* | (2006.01) |
| *A61K 31/454* | (2006.01) |
| *A61P 21/00* | (2006.01) |

(52) U.S. Cl.
CPC .......... *A61K 31/138* (2013.01); *A61K 31/454* (2013.01); *A61K 31/4535* (2013.01); *A61K 45/06* (2013.01); *A61P 21/00* (2018.01)

(58) Field of Classification Search
None
See application file for complete search history.

(56) References Cited

PUBLICATIONS

Dorchies et al. The American Journal of Pathology 182(2), 485-204 (2013) (Year: 2013).*
Blaeser et al. "Mouse models of fukutin-related protein mutations show a wide range of disease phenotypes" *Human Genetics* 132:923-934 (2013).
Brockington et al. "Mutations in the Fukutin-Related Protein Gene (FKRP) Cause a Form of Congenital Muscular Dystrophy with Secondary Laminin α2 Deficiency and Abnormal Glycosylation of α-Dystroglycan" *The American Journal of Human Genetics* 69:1198-1209 (2001).
Carss et al. "Mutations in GDP-Mannose Pyrophosphorylase B Cause Congenital and Limb-Girdle Muscular Dystrophies Associated with Hypoglycosylation of α-Dystroglycan" *The American Journal of Human Genetics* 93:29-41 (2013).
Chan et al. "Fukutin-related protein is essential for mouse muscle, brain and eye development and mutation recapitulates the wide clinical spectrums of dystroglycanopathies" *Human Molecular Genetics* 19(20):3995-4006 (2010).
Gee et al. "Dystroglycan-α, a dystrophin-associated glycoprotein, is a functional agrin receptor" *Cell* 77(5):675-686 (1994) (Abstract only).
Kobayashi et al. "An ancient retrotransposal insertion causes Fukuyama-type congenital muscular dystrophy" *Nature* 394:388-392 (1998) (Abstract only).
Lefeber et al. "Deficiency of Dol-P-Man Synthase Subunit DPM3 Bridges the Congenital Disorders of Glycosylation with the Dystroglycanopathies" *The American Journal of Human Genetics* 85:76-86 (2009).
Lefeber et al. "Autosomal Recessive Dilated Cardiomyopathy due to DOLK Mutations Results from Abnormal Dystroglycan O-Mannosylation" *PLoS Genetics* 7(12):e1002427 (2011).
Longman et al. "Mutations in the human LARGE gene cause MSC1D, a novel form of congenital muscular dystrophy with severe mental retardation and abnormal glycosylation of α-dystroglycan" *Human Molecular Genetics* 12(21):2853-2861 (2003).
Manzini et al. "Exome Sequencing and Functional Validation in Zebrafish Identify GTDC2 Mutations as a Cause of Walker-Warburg Syndrome" *The American Journal of Human Genetics* 91:541-547 (2012).
Roscioli et al. "Mutations in ISPD cause Walker-Warburg syndrome and defective glycosylation of α-dystroglycan" *Nature Genetics* 44(5):581-585 (2012).
Stevens et al. "Mutations in B3GALNT2 Cause Congenital Muscular Dystrophy and Hypoglycosylation of α-Dystroglycan" *The American Journal of Human Genetics* 92:354-365 (2013).
Van Reeuwijk et al. "POMT2 mutations cause α-dystroglycan hypoglycosylation and Walker-Warbug syndrome" *Journal of Medical Genetics* 42:907-912 (2005).
Vuillaumier-Barrot et al. "Identification of Mutations in TMEM5 and ISPD as a Cause of Severe Cobblestone Lissencephaly" *The American Journal of Human Genetics* 91:1135-1143 (2012).
Yoshida-Moriguchi et al. "SGK196 Is a Glycosylation-Specific O-Mannose Kinase Required for Dystroglycan Function" *Science* 341(6148):1-10 (2013).

* cited by examiner

*Primary Examiner* — Dennis Heyer
(74) *Attorney, Agent, or Firm* — Myers Bigel, P.A.

(57) ABSTRACT

The present invention provides compositions and methods of their use in treating dystroglycanopathy, muscular dystrophy and other disorders.

9 Claims, 6 Drawing Sheets

COMPOUNDS AND METHODS FOR TREATING MUSCULAR DYSTROPHY AND OTHER DISORDERS

STATEMENT OF PRIORITY

This application claims the benefit, under 35 U.S.C. § 119(e), of U.S. Provisional Application No. 62/450,451, filed Jan. 25, 2017, the entire contents of which are incorporated by reference herein.

FIELD OF THE INVENTION

The present invention is directed to pharmaceutical formulations and methods of use thereof in treating dystroglycanopathy, muscular dystrophy and other disorders.

BACKGROUND OF THE INVENTION

Dystroglycanopathies are a subset of muscular dystrophies characterized by a secondary defect in glycosylation of alpha-dystroglycan (α-DG). The diseases have been linked to autosomal-recessive mutations in at least 18 different genes. They include fukutin-related protein (FKRP), fukutin, like-acetylglucosaminyltransferase (LARGE), POMGnT1, POMT1, POMT2, Isoprenoid Synthase Domain Containing (ISPD), Transmembrane protein 5 (TMEM5), β1,3-N-acetylglucosaminyltransferase1 (B3GNT1), glycosyltransferase-like domain containing 2 (GTDC2), β3-N-acetylgalactosaminyltransferase 2 (B3GALNT2) DOLK, GMPPB, DMP2, DMP3 and SGK196. Biochemical studies have established direct evidence for involvement of a number of the genes in glycosylation modifications of α-DG. Fukutin and Fukutin related protein (FKRP) have been recently proposed as Ribitol-5-P transferases that transfer the phosphorated ribitol to the core sugar chain of α-DG. LARGE protein acts as a bifunctional glycosyltransferase, xylosyltransferase and glucuronyltransferase, producing repeating units of [-3-xylose-α1,3-glucuronic acid-β1-] that is the functional glycan chain linking cell membrane protein and extracellular matrix proteins. This LARGE glycan chain is linked to the core O-mannosyl glycans by tandem ribitols. This linkage is critical for muscle health and lack of FKRP function as the result of gene mutations therefore prevents the production of functional glycosylation of α-DG, and disrupts normal interaction between membrane and connective tissues, leading to muscle fiber damage and muscular dystrophy.

Mutations in the FKRP gene cause a wide spectrum of disease from a milder form of limb-girdle muscular dystrophy type 2I (LGMD2I) to severe Walker-Warburg syndrome (WWS), muscle-eye-brain disease (MEB), and congenital muscular dystrophy type 1D (MDC1D). However, little progress has been made for the treatment of the diseases. There is no effective therapy available and only physical therapy and palliative care are being routinely provided as treatment.

The present invention overcomes previous shortcomings in the art by providing pharmaceutical compositions and methods of their use in treating dystroglycanopathy, muscular dystrophy and other disorders.

SUMMARY OF THE INVENTION

In one aspect, the present invention provides a method of maintaining and/or improving muscle function in a subject that has or is at increased risk of having dystroglycanopathy, comprising administering to the subject an effective amount of a selective estrogen receptor modulator (SERM), thereby maintaining and/or improving muscle function in the subject.

In a further aspect, the present invention provides a method of reducing and/or reversing muscle pathology in a subject that has or is at increased risk of having dystroglycanopathy, comprising administering to the subject an effective amount of a selective estrogen receptor modulator (SERM), thereby reducing and/or reversing muscle pathology in the subject.

Further provided herein is a method of treating muscular dystrophy associated with defective glycosylation of α-DG in a subject, comprising administering to the subject an effective amount of a SERM, thereby treating the muscular dystrophy in the subject.

The present invention additionally provides a method of treating a disorder in a subject associated with a mutation in a fukutin related protein (FKRP) gene, comprising administering to the subject an effective amount of a SERM, thereby treating the disorder in the subject.

In another aspect, the present invention provides a method of treating or inhibiting the development of muscle weakness in a subject that is a carrier of a mutated FKRP gene, comprising administering to the subject an effective amount of a SERM, thereby treating or inhibiting the development of muscle weakness in the subject.

Also provided herein is a method of maintaining and/or improving muscle function in a subject that has or is at increased risk of having muscular dystrophy, comprising administering to the subject an effective amount of a selective estrogen receptor modulator (SERM), thereby maintaining and/or improving muscle function in the subject.

The present invention is explained in greater detail below.

DETAILED DESCRIPTION OF THE INVENTION

Figure 1:
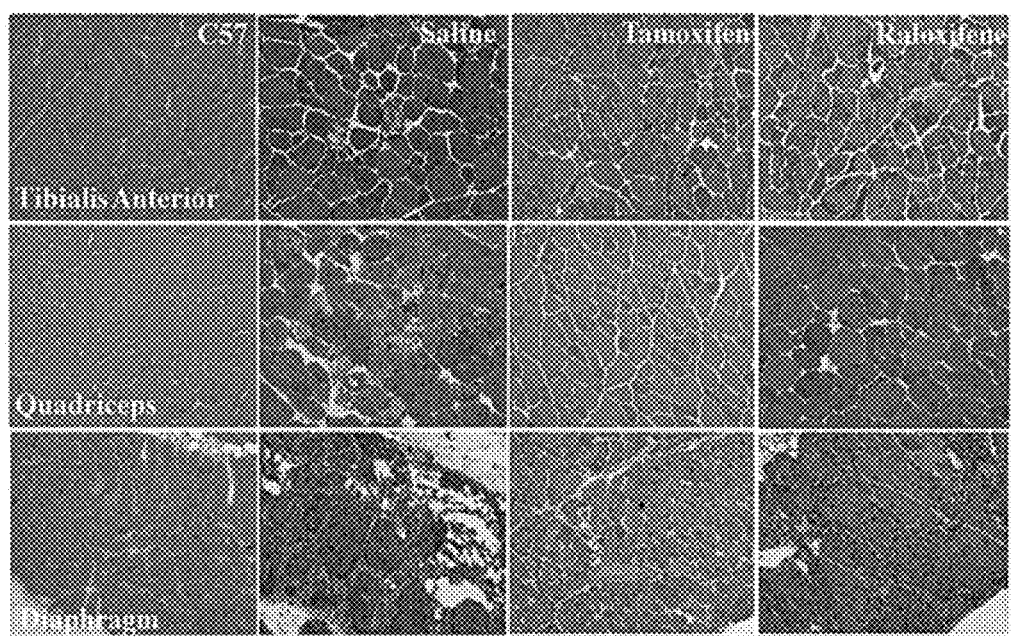
FIG. 1. Selective estrogen receptor modulators (SERMs) tamoxifen and raloxifene significantly improve muscle pathology after a 6 month treatment (5 days a week, 10 mg/kg). C57 normal mouse muscles were used as controls. Saline, mice treated with saline as negative control. Reduction in inflammation, degeneration and fibrotic tissue were clearly demonstrated in both raloxifene and tamoxifen treated muscles. Hematoxylin and eosin (H&E) staining was used.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which does not depart from the instant invention. Hence, the following specification is intended to illustrate some particular embodiments of the invention, and not to exhaustively specify all permutations, combinations and variations thereof.

The disclosures of all patents, patent publications and non-patent documents cited herein are incorporated herein by reference in their entirety.

The present invention is based on the unexpected discovery that selective estrogen receptor modulators (SERMs) are effective in the treatment of dystroglycanopathy, and that tamoxifen and raloxifene treatment in particular significantly improve muscle pathology and function and this is associated with enhanced glycosylation of alpha-dystroglycan ($\alpha$-DG).

Thus, in one embodiment, the present invention provides a method of maintaining and/or improving muscle function in a subject that has or is at increased risk of having a dystroglycanopathy, comprising administering to the subject an effective amount of a selective estrogen receptor modulator (SERM), thereby maintaining and/or improving muscle function in the subject.

The present invention further provides a method of reducing and/or reversing muscle pathology in a subject that has or is at increased risk of having a dystroglycanopathy, comprising administering to the subject an effective amount of a selective estrogen receptor modulator (SERM), thereby reducing and/or reversing muscle pathology in the subject.

Additionally provided herein is a method of treating muscular dystrophy associated with defective glycosylation of $\alpha$-DG in a subject, comprising administering to the subject an effective amount of a SERM, thereby treating the muscular dystrophy in the subject.

In further embodiments, the present invention provides a method of treating a disorder in a subject associated with a mutation in a fukutin related protein (FKRP) gene, comprising administering to the subject an effective amount of a SERM, thereby treating the disorder in the subject.

The present invention also provides a method of treating or inhibiting the development of muscle weakness in a subject that is a carrier of a mutated FKRP gene, comprising administering to the subject an effective amount of a SERM, thereby treating or inhibiting the development of muscle weakness in the subject.

Additionally provided herein is a method of maintaining and/or improving muscle function in a subject that has or is at increased risk of having muscular dystrophy, comprising administering to the subject an effective amount of a selective estrogen receptor modulator (SERM), thereby maintaining and/or improving muscle function in the subject.

In the methods described herein, in particular embodiments, the muscle weakness can be in skeletal muscle, cardiac muscle and/or respiratory muscle, singly or in any combination.

In the methods described herein, the disorder associated with a mutation or loss of function in the FKRP gene can be, but is not limited to, limb-girdle muscular dystrophy (LGMD2I), Walker-Warburg syndrome (WWS), muscle-eye-brain disease (MEB), congenital muscular dystrophy type 1C (MDC1C), congenital muscular dystrophy type 1D (MDC1D), and any combination thereof.

In the methods of this invention, the selective estrogen receptor modulator (SERM) can be, but is not limited to, tamoxifen, raloxifene, methyl-piperidino-pyrazole (MPP) and any combination thereof.

The method of this invention can include a step of additionally administering to the subject a therapeutic agent, in combination with the SERM (concurrently, before and/or after SERM administration). Nonlimiting examples of a therapeutic agent of this invention include a phosphodiesterase type 5 (PDE 5) inhibitor, a nonsteroidal anti-inflammatory agent, a metabolite supplement, or any combination thereof.

In some embodiments, the SERM can be co-administered with (prior to, simultaneously and/or after) a bisphosphonate (e.g., Alendronate), an angiotensin converting enzyme inhibitor (ACE inhibitor), an angiotensin receptor blocker (e.g., rosartan), singly or in any combination. Furthermore, in the methods of this invention, a SERM can be administered with any other therapy and/or therapeutic agent (simultaneously, before and/or after), such as steroid therapy and/or FKRP gene therapy to enhance or increase the therapeutic effect.

In some embodiments, the subject of this invention is a female subject and in some embodiments, the subject of this invention is a male subject. In particular embodiments, the SERM is tamoxifen and the subject is a female subject. In other embodiments, the SERM is raloxifene and the subject is a male or female subject that has or is at increased risk of having muscular dystrophy.

The methods of this invention can also be used to treat non-muscular dystrophy diseases for which restoration of and/or enhanced glycosylation of α-DG would be beneficial and/or therapeutic.

In some embodiments, the active compound of this invention (e.g., SERM) can comprise a polyalkylene glycol moiety coupled or linked thereto. "Polyalkylene glycol" means straight or branched polyalkylene glycol polymers including, but not limited to, polyethylene glycol (PEG), polypropylene glycol (PPG), and polybutylene glycol (PBG), as well as co-polymers of PEG, PPG and PBG in any combination, and includes the monoalkylether of the polyalkylene glycol. Thus, in various embodiments of this invention, the polyalkylene glycol in the compositions of this invention can be, but is not limited to, polyethylene glycol, polypropylene glycol, polybutylene glycol, and any combination thereof.

In certain embodiments, the polyalkylene glycol of the composition is polyethylene glycol or "PEG." The term "PEG subunit" refers to a single polyethylene glycol unit, i.e., $-(CH_2CH_2O)-$. Thus, the active compound can be "pegylated." In some embodiments, the PEG can have a molecular weight from about 10,000 g/mol to about 30,000 g/mol.

In some embodiments, the polyalkylene glycol (e.g., PEG) can be non-polydispersed, monodispersed, substantially monodispersed, purely monodispersed, or substantially purely monodispersed.

"Monodispersed" is used to describe a mixture of compounds wherein about 100 percent of the compounds in the mixture have the same molecular weight.

"Substantially monodispersed" is used to describe a mixture of compounds wherein at least about 95 percent of the compounds in the mixture have the same molecular weight.

"Purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture.

"Substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture.

Further aspects of this invention include the use of a SERM and/or a composition of this invention in the preparation of a medicament for carrying out the methods of this invention.

An additional aspect is the use of a SERM and/or a composition of this invention for carrying out the methods of this invention.

The SERM of this invention can be in a composition comprising a pharmaceutically acceptable carrier. The therapeutically effective amount or dosage of a SERM or composition of this invention will vary depending on the subject's condition and therapeutic need, and will also depend, among other things, upon the effect or result to be achieved, the status of the subject and/or the route and/or mode of delivery. In some embodiments, The drug can be mixed or combined with any substance for improved delivery, absorption, etc.

Administration of the compound or composition of this invention may be by any suitable route, including but not limited to intrathecal injection, subcutaneous, cutaneous, oral, intravenous, intraperitoneal, intramuscular injection, intra-arterial, intratumoral or any intratissue injection, nasal, oral, sublingual, via inhalation, in an implant, in a matrix, in a gel, or any combination thereof.

Definitions

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising."

"Subject" as used herein includes any animal in which functional glycosylation of alpha-dystroglycan (α-DG) and/or treatment of muscular dystrophy is necessary or desired. In some embodiments, the subject is any animal that can receive a beneficial and/or therapeutic effect from restoration of functional glycosylation of alpha-dystroglycan (α-DG) and/or enhancement of glycosylation of α-DG. In some embodiments, the subject is a mammal and in particular embodiments, the subject is a human of any age, race, gender, or ethnicity, etc. In particular embodiments, the subject is a female human. In particular embodiments, the subject is a male human.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay or inhibition in the progression of the disease or disorder.

"Treat," "treating" or "treatment" as used herein also refers to any type of action or administration that imparts a benefit to a subject that has a disease or disorder, including improvement in the condition of the patient (e.g., reduction or amelioration of one or more symptoms), healing, etc.

The terms "therapeutically effective amount," "treatment effective amount" and "effective amount" as used herein are synonymous unless otherwise indicated, and mean an amount of a compound, peptide or composition of the present invention that is sufficient to improve the condition, disease, or disorder being treated and/or achieved the desired benefit or goal (e.g., control of body weight). Those skilled in the art will appreciate that the therapeutic effects need not be complete or curative, as long as some benefit is provided to the subject.

Determination of a therapeutically effective amount, as well as other factors related to effective administration of a compound of the present invention to a subject of this invention, including dosage forms, routes of administration, and frequency of dosing, may depend upon the particulars of the condition that is encountered, including the subject and condition being treated or addressed, the severity of the condition in a particular subject, the particular compound being employed, the particular route of administration being employed, the frequency of dosing, and the particular formulation being employed. Determination of a therapeutically effective treatment regimen for a subject of this invention is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the subject being treated and the particular mode of administration.

In some embodiments, a SERM of this invention (e.g., tamoxifen and/or raloxifene) can be delivered orally or intravenously or subcutaneously to a subject of this invention daily, weekly, biweekly or monthly in a dosage range of about 0.01 mg/kg to about 100 mg/kg (e.g., 0.01. 0.05. 0.075, 0.1, 0.2, 0.3, 0.4, 0.5, 0.6, 0.7, 0.8, 0.9. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 mg/kg) per treatment. Nonlimiting examples of dosage ranges of this invention include from about 0.01 mg/kg to about 0.1 mg/kg, from about 1 mg/kg to about 10 mg/kg, from about 10 mg/kg to about 50 mg/kg a day, etc. In some embodiments, for daily use, the dose can range from about 0.01 mg/kg to about 0.1 mg/kg, or from about 1 mg/kg to about 10 mg/kg a day. In some embodiments, e.g., for weekly or monthly treatment, the dose can range from about 0.1 mg/kg to about 1 mg/kg or from about 10 mg/kg to about 50 mg/kg per treatment.

As used herein, "modulate," "modulates" or "modulation" refers to enhancement (e.g., an increase) or inhibition (e.g., diminished, reduced or suppressed) of the specified activity.

The term "enhancement," "enhance," "enhances," or "enhancing" refers to an increase in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or an increase in the specified activity of at least about 5%, 10%, 25%, 35%, 40%, 50%, 60%, 75%, 80%, 90%, 95%, 97%, 98%, 99% or 100%.

The term "inhibit," "diminish," "reduce" or "suppress" refers to a decrease in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or a decrease or reduction in the specified activity of at least about 5%, 10%, 25%, 35%, 40%, 50%, 60%, 75%, 80%, 90%, 95%, 97%, 98%, 99% or 100%. These terms are intended to be relative to a reference or control.

The above terms are relative to a reference or control. For example, in a method of maintaining and/or improving muscle function in a subject that has or is at increased risk of having dystroglycanopathy, comprising administering to the subject an effective amount of a selective estrogen receptor modulator (SERM), the maintenance or improvement is relative to the amount of muscle function in a subject (e.g., a control subject) in the absence of administration of a SERM. As another example, in a method of reducing and/or reversing muscle pathology in a subject that has or is at increased risk of having dystroglycanopathy, comprising administering to the subject an effective amount of a selective estrogen receptor modulator (SERM), the reduction or reversal is relative to the amount of muscle pathology in a subject (e.g., a control subject) in the absence of administration of a SERM.

"Isolated" as used herein means the SERM of this invention is sufficiently free of contaminants or cell components with which SERMs may occur. "Isolated" does not mean that the preparation is technically pure (homogeneous), but it is sufficiently pure to provide the SERM in a form in which it can be used therapeutically.

The term "prevent," "preventing" or "prevention of" (and grammatical variations thereof) refers to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression are less than what would occur in the absence of carrying out the steps of the methods of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

"Concurrently administering" or "concurrently administer" as used herein means that the two or more compounds or compositions are administered closely enough in time to produce a combined effect (that is, concurrently may be simultaneously, or it may be two or more events occurring within a short time period before and/or after each other, e.g., sequentially). Simultaneous concurrent administration may be carried out by mixing the compounds prior to administration, or by administering the compounds at the same point in time but at different anatomic sites and/or by using different routes of administration.

"Pharmaceutically acceptable" as used herein means that the compound or composition is suitable for administration to a subject to achieve the treatments described herein, without unduly deleterious side effects in light of the severity of the disease and necessity of the treatment.

Pharmaceutical Formulations.

The active compounds described herein may be formulated for administration in a pharmaceutical carrier in accordance with known techniques. See, e.g., Remington, *The Science and Practice of Pharmacy* (21$^{st}$ Ed. 2005). In the manufacture of a pharmaceutical formulation according to the invention, the active compound is typically admixed with, inter alia, an acceptable carrier. The carrier must, of course, be acceptable in the sense of being compatible with any other ingredients in the formulation and must not be deleterious to the subject. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as saline solutions, water, emulsions such as oil/water emulsion, microemulsions and various types of wetting agents.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In some embodiments of this invention, the compound of this invention is present in an aqueous solution for subcutaneous administration. In some embodiments, the compound is provided as a lyophilized powder that is reconstituted and administered subcutaneously.

The present invention is illustrated in the following non-limiting examples.

EXAMPLES

This invention identifies the use of a selective estrogen receptor modulator (SERM) for dystroglycanopathy, including specific embodiments using tamoxifen and raloxifene, which significantly improves muscle pathology and function and this is associated with enhanced glycosylation of alpha-dystroglycan detected by specific antibodies that bind the functional part of the sugar component.

Both tamoxifen and raloxifene have estrogen-like (agonist) effect and antiestrogen (antagonist) effect on tissues, but the effects vary significantly among different tissues. As a result, both have very wide variations in effect on metabolism, function and tissue repair in different tissues. The drugs have been most widely used for breast cancer treatment and prevention. They have also been used for postmenopausal hormone replacement therapy (HRT), osteoporosis, and muscle regeneration. Reported other benefits include fat reduction, reduction in cholesterol levels, and anti-fibrosis effect. The main side effects for long term use include higher risk of endometrial cancer and thromboembolism.

Dystroglycanopathy defines a group of specific muscular dystrophies with different genetic defects and a characteristic protein expression profile that is widely different from Duchenne muscular dystrophy (DMD). Lack of dystrophin is the cause for DMD, whereas lack of functional glycosylated alpha-dystroglycan is the direct cause for dystroglycanopathies.

Currently, no specific treatment is available for FKRP-related diseases or any of the glycosylation deficient muscular dystrophies. Glucocorticoid steroids (steroids) have been reported for the alleviation of disease symptoms with limited benefit, largely based on results from reported uses to treat Duchenne muscular dystrophy. Therapeutic potential is believed to be achieved through its anti-inflammatory effects. However, benefits of steroids in the treatment of any muscular dystrophy often last only a limited time period and are always associated with severe side effects, including dramatic weight gain and reduction in bone mineral density, osteoporosis and growth retardation. Physical therapy and palliative care are routinely provided but only serve to relieve symptoms and are unable to delay disease progression. Currently there are several potential therapies, including AAV gene therapy and gene correction in preclinical development for dystroglycanopathies, but none of them has entered clinic trials.

The use of a virus for gene therapy and gene editing has demonstrated the capability of achieving a systemic effect with improved muscle pathology and functions, and even a complete halt of disease progression in animal models of many different types of muscular dystrophies. However, all gene therapy drugs remain in preclinic and clinic trial stages. Further, their efficacy in the clinic remains to be proved. No SERM drug-related therapy for dystroglycanopathy has been tested or trialed.

All available treatments, including the use of steroids and physical therapy can only achieve relief of symptoms, such as inflammation and pain, but cannot effectively delay disease progression.

Use of a virus in gene therapy protocols to treat FKRP-related diseases remains to be trialed in patients for efficacy. Viral vector associated risks include immune response to viral proteins, non-target tissue expression of transgene, long-term toxicity of the overexpressed gene product and alteration of genomic sequence. These potential risks delay the progress in clinical trials. These risks are further amplified by the requirement of using extremely large quantities of virus for systemic delivery to achieve effective treatment for muscular dystrophy. Therefore the long-term outcome of virus mediated treatment remains to be investigated and cannot be easily determined. Non-viral gene delivery remains insufficient for achieving therapeutic value even in animal models.

Figure 2:
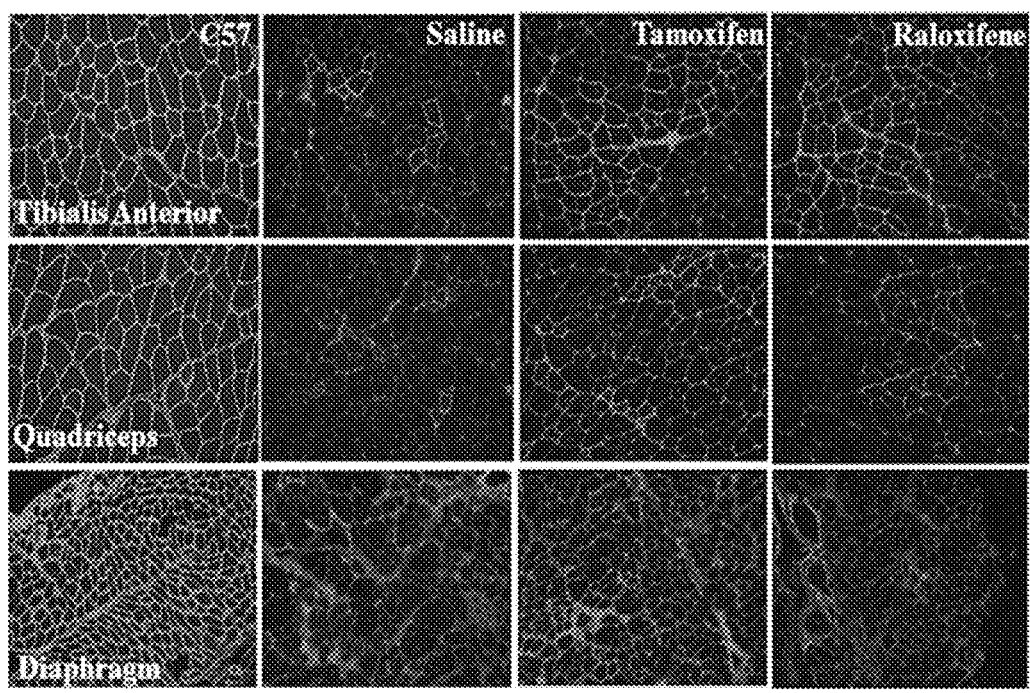
FIG. 2. Selective estrogen receptor modulators (SERMs) tamoxifen and raloxifene enhance the levels of glycosylated alpha-dystroglycan (α-DG) detected by immunohistochemistry with the monoclonal antibody IIH6 after 6 months of treatment (5 days a week, 10 mg/kg). C57 normal mouse muscles were used as controls. Saline, mice treated with saline as negative control. The positive staining is seen surrounding the fiber membrane and a few revertant fibers are observed in the saline treated controls. The number of IIH6 positive fibers is clearly increased in the treated muscles.
Figure 3:
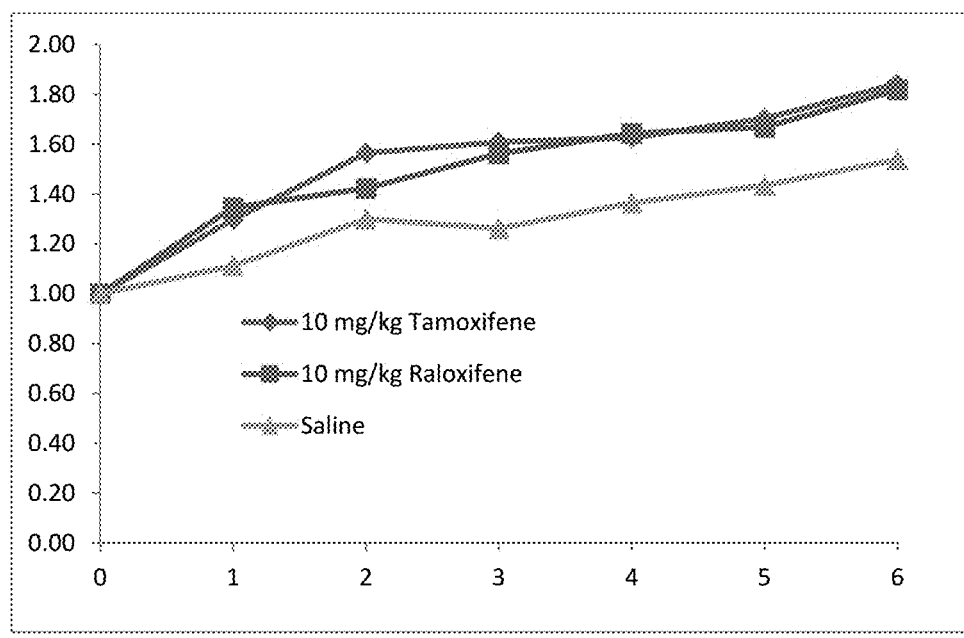
FIG. 3. Selective estrogen receptor modulators (SERMs) tamoxifen and raloxifene improve muscle function, as shown with grip force measurement after 6 months of treatment (5 days a week, 10 mg/kg). C57 normal mice muscles as controls. Saline, mice treated with saline as negative control.
Figure 4:
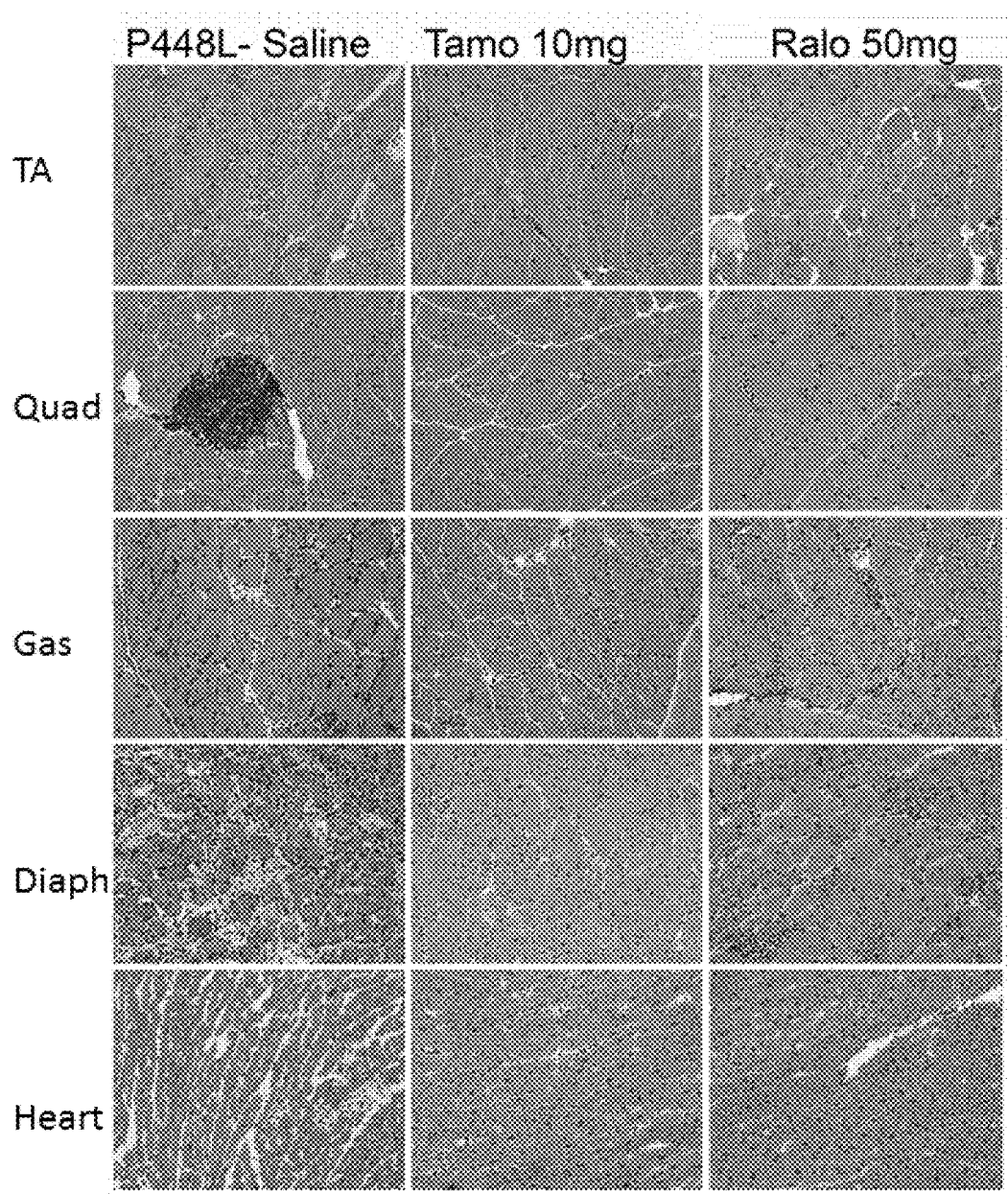
FIG. 4. Improvement in histology of P448L mutant mice after 1 year of treatment with selective estrogen receptor modulators (SERMs) tamoxifen (10 mg/kg/day, 5 day a week) and raloxifene (50 mg/kg/day, 5 day a week). H&E staining was used. The therapeutic effect is best seen with 10 mg/kg tamoxifen treatment. Reduction in inflammation, degeneration and fibrotic tissue were clearly demonstrated in the skeletal muscle of both raloxifene and tamoxifen treated muscles. Reduced fibrotic streaks are also observed in the treated cardiac muscles. C57 normal mouse muscles were used as controls. P448-Saline, mice treated with saline as negative control.
Figure 5:
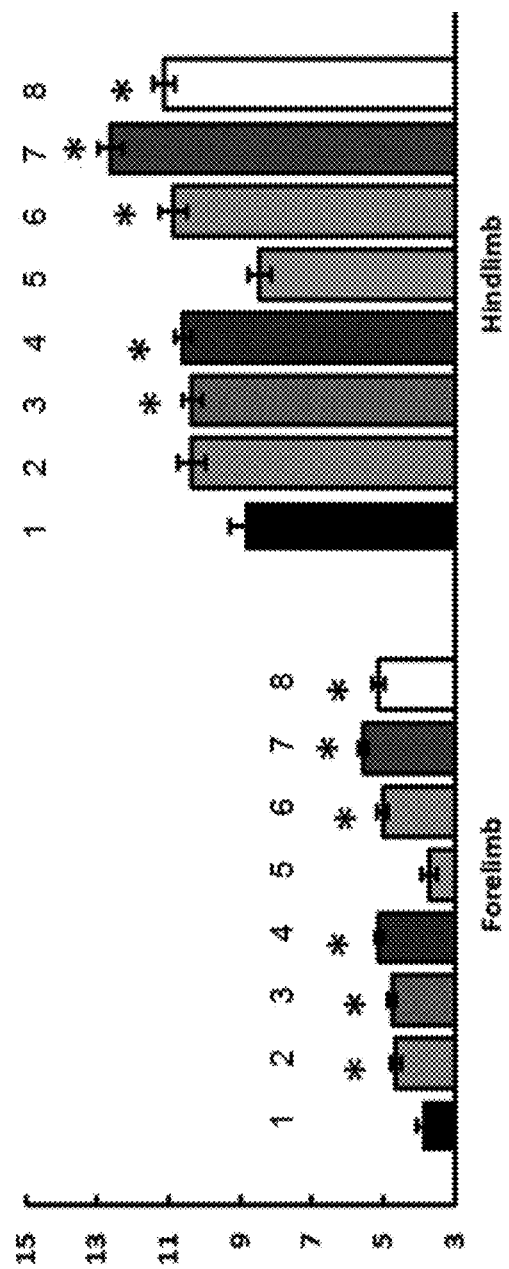
FIG. 5. Significant improvement in grip force measurement is observed in the mice treated with tamoxifen (2 mg/kg/day, 10 mg/kg/day and 50 mg/kg/day, columns 2, 3 and 4, respectively) and raloxifene (50 mg/kg/day and 100 mg/kg/day, columns 6 and 7, respectively), except for the hindlimb in the 2 mg/kg tamoxifen treated cohort, which did not reach significance when compared to the saline-treated cohort. Saline treated control, column 1; C57 normal control, column 8). Treatment with 10 mg/kg tamoxifen in combination with 5 mg/kg prednisolone (column 5) does not improve muscle function.
Figure 6:
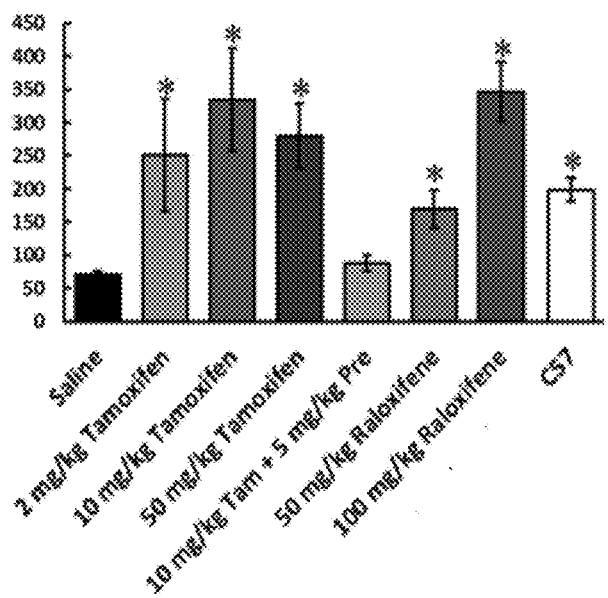
FIG. 6. Significant improvement in treadmill exercise is observed for both running time and distance in the mice treated with tamoxifen (2 mg/kg/day, 10 mg/kg/day and 50 mg/kg/day, Columns 2, 3 and 4, respectively) and raloxifene (50 mg/kg/day and 100 mg/kg/day, Columns 6 and 7, respectively), except for the running time in the 2 mg/kg tamoxifen treated cohort, which did not reach significance when compared to the saline-treated cohort. Saline treated control, column 1; C57 normal control, column 8). Treatment with 10 mg/kg tamoxifen in combination with 5 mg/kg prednisolone (column 5) does not improve muscle function.
Figure 6:
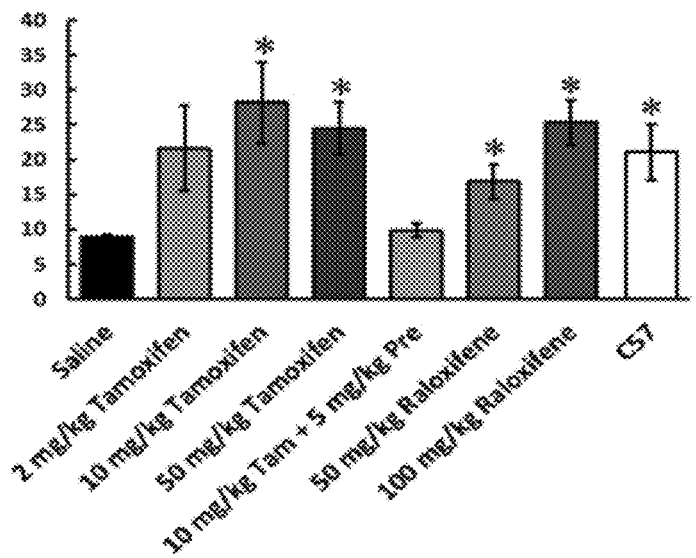

This invention applies tamoxifen and raloxifene for clinical use in FKRP mutant dystrophic mouse models for the treatment of dystroglycanopathies, specifically those caused by mutations in the FKRP gene. Mutations in the FKRP gene cause muscular dystrophy with the lack of functional glycosylation of alpha-dystroglycan ($\alpha$-DG) as the characteristic biochemical marker in the diseased tissues. Mouse models with the FKRP mutations present in patients show the same biochemical feature as patients' tissues, most prominently in muscles (Chan Y M, *Hum Mol Genet* 2010, 19(20): 3995-4006; Blaeser A, *Hum Genet* 2013, 132(8): 923-934). Using immunohistochemistry with the antibody, IIH6, which is specific to the functional glycosylated $\alpha$-DG, it was shown that muscle fibers from both skeletal and cardiac muscles of the P448L FKRP mutant mice produce significantly decreased amounts to almost no functional glycosylated $\alpha$-DG. This can also be demonstrated by western blot detection. Histologically, the diseased muscles undergo continuous degeneration as indicated by the presence of degenerating muscle fibers, variation in fiber size, presence of centrally nucleated fibers (a result of regeneration which is the consequence of muscle damage), inflammatory cells and an increase in non-muscle fiber connective tissues (FIG. 1). Surprisingly, feeding FKRP-P448L mutant dystrophic mice with tamoxifen and raloxifene 5 days a week significantly improved muscle pathology and function. The therapeutic effects are dose-related with increasing efficacy from 2 mg/kg/day, 5 mg/kg/day, 10 mg/kg/day, to 50 mg/kg/day for tamoxifen, and from 10 mg/kg/day, 50 mg/kg/day and 100 mg/kg/day for raloxifene. The best results were obtained with 5-10 mg/kg tamoxifen and 50 mg/kg raloxifene, which would be equivalent to human equivalent dose (HED) of about 0.5 mg/kg for tamoxifen and 5 mg/kg for raloxifene. Most surprisingly, our results show that the muscles from tamoxifen-treated mice have enhanced expression of alpha-DG (FIG. 2) and improved muscle function (FIG. 3). All the results therefore suggest that the SERM-modulated glycosylation of α-DG is probably one of the mechanisms by which the treated diseased muscles improve their pathology and function. The improvement in muscle function and pathology is even greater after 1 year treatment. This includes significant improvement of muscle pathology and function (FIGS. 4-6).

The drugs, tamoxifen and raloxifene, can be delivered orally, intravenously and/or subcutaneously, singly or in any combination, on a daily, weekly, biweekly or monthly schedule. Exemplary doses can be from about 0.01 mg/kg to 0.1 mg/kg, 1 mg/kg to 10 mg/kg, or 10 mg/kg to 50 mg/kg a day. For daily use, the doses can range, e.g., from about 0.01 mg/kg to about 0.1 mg/kg, or from about 1 mg/kg to about 10 mg/kg a day. For weekly or monthly treatment regimen, the doses can range, e.g., from about 0.1 mg/kg to about 1 mg/kg, or from about 10 mg/kg to about 50 mg/kg per treatment.

The drugs can be administrated to individuals with dystroglycanopathies caused by mutations of known and unknown genes. The drugs can also be administered to individuals with dystroglycanopathy-related mutations in a single allele, i.e., the individual is a heterozygote with one normal copy of the gene and without obvious or apparent muscular dystrophy or other symptoms. For such individuals, the drug can be delivered in any way described as for muscular dystrophy patients preferably with reduced dosage.

SERMs are groups of selective estrogen receptor modulators. It is likely that modification of any specific SERM, including tamoxifen or raloxifene could further enhance its therapeutic potential in treating dystroglycanopathy. It is also possible that other members of the SERM family, such as MPP, could have significant therapeutic effect.

This is the first time, to the inventor's knowledge, that these drugs have been tested in animal models of dystroglycanopathy, and specifically in mouse model of FKRP mutation-related dystroglycanopathy. It is surprising that the drugs can have a significant effect on diseased muscle and on muscle function. It is also surprising that both tamoxifen and raloxifene have significant therapeutic value on the disease. Furthermore, it is a surprising discovery that these drugs have an effect on glycosylation of a-DG, which is the critical link between muscle fiber and extracellular matrix.

Although the present process has been described with reference to specific details of certain embodiments thereof, it is not intended that such details should be regarded as limitations upon the scope of the invention except as and to the extent that they are included in the accompanying claims.

Throughout this application, various patents and non-patent publications are referenced. The disclosures of these patents and publications in their entireties are hereby incorporated by reference into this application in order to more fully describe the state of the art to which this invention pertains.

That which is claimed is:

1. A method of treating a disorder associated with a mutation or loss of function in a fukutin related protein (FKRP) gene in a subject, wherein the disorder is selected from the group consisting of limb-girdle muscular dystrophy type 2I (LGMD2I), Walker-Warburg syndrome (WWS), muscle-eye-brain disease (MEB), congenital muscular dystrophy type 1C (MDC1C), congenital muscular dystrophy type 1D (MDC1D), and any combination thereof, comprising administering to the subject an effective amount of a selective estrogen receptor modulator (SERM), thereby treating the disorder in the subject.

2. A method of treating or inhibiting the development of muscle weakness in a subject that is a carrier of a mutated FKRP gene, wherein the muscle weakness is caused by limb-girdle muscular dystrophy type 2I (LGMD2I), Walker-Warburg syndrome (WWS), muscle-eye-brain disease (MEB), congenital muscular dystrophy type 1C (MDC1C), congenital muscular dystrophy type 1D (MDC1D), and any combination thereof, comprising administering to the subject an effective amount of a SERM, thereby treating or inhibiting the development of muscle weakness in the subject.

3. The method of claim 2, wherein the muscle weakness is in muscle selected from the group consisting of skeletal muscle, cardiac muscle, respiratory muscle, and any combination thereof.

4. The method of claim 1, wherein the SERM is selected from the group consisting of tamoxifen, raloxifene, methyl-piperidino-pyrazole (MPP) and any combination thereof.

5. The method of claim 1, further comprising additionally administering to the subject an effective amount of a therapeutic agent.

6. The method of claim 5, wherein the therapeutic agent is a phosphodiesterase type 5 (PDE 5) inhibitor, a nonsteroidal anti-inflammatory agent, a metabolite supplement, or any combination thereof.

7. The method of claim 2, wherein the SERM is selected from the group consisting of tamoxifen, raloxifene, methyl-piperidino-pyrazole (MPP) and any combination thereof.

8. The method of claim 2, further comprising additionally administering to the subject an effective amount of a therapeutic agent.

9. The method of claim 8, wherein the therapeutic agent is a phosphodiesterase type 5 (PDE 5) inhibitor, a nonsteroidal anti-inflammatory agent, a metabolite supplement, or any combination thereof.

* * * * *